US00PP30645P3

(12) United States Plant Patent
Suphachadiwong

(10) Patent No.: US PP30,645 P3
(45) Date of Patent: Jul. 2, 2019

(54) ***VANDA* PLANT NAMED 'SPCDW1705'**

(50) Latin Name: ***Vanda* spp. Jones ex R. Br.**
Varietal Denomination: SPCDW1705

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 0 days.

(21) Appl. No.: 15/998,365

(22) Filed: Aug. 9, 2018

(65) Prior Publication Data

US 2019/0053412 P1 Feb. 14, 2019

(30) Foreign Application Priority Data

Aug. 9, 2017 (QZ) ..... PBR 2017/1986

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./263.1, 311
See application file for complete search history.

*Primary Examiner* — Susan McCormick Ewoldt
*Assistant Examiner* — Karen M Redden
(74) *Attorney, Agent, or Firm* — Samuel R. McCoy, Jr.

(57) ABSTRACT

A new and distinct *Vanda* plant named 'SPCDW1705' which is characterized by large flowers with broad, reniform to orbicular flower petals and broad ovate sepals, petals and sepals that are moderately to strongly overlapping, petals and sepals with moderately to strongly undulated margins, light purple petals and sepals that are heavily dotted and blotched with a mixture of violet and violet-purple, a labellum with a very dark violet-blue central lobe and light yellow lateral lobes which are dotted violet-blue, and the stability of these characteristics from generation to generation.

4 Drawing Sheets

Latin name of the genus and species: The Latin name of the genus and species of the novel variety disclosed herein is *Vanda* spp. Jones ex R. Br.

Variety denomination: The inventive variety of *Vanda* disclosed herein has been given the variety denomination 'SPCDW1705'.

CROSS REFERENCE TO RELATED APPLICATIONS

This application claims priority to the Community Plant Variety Rights application number 2017/1986, filed Aug. 9, 2017, which is herein incorporated by reference.

BACKGROUND OF THE INVENTION

Parentage: The new *Vanda* plant, 'SPCDW1705', is the result of a planned breeding program. 'SPCDW1705' originated as a seedling from the controlled pollination of *Vanda* 'S13' (not patented), the seed parent, with *Vanda* 'NJR' (not patented), the pollen parent. Both parents were developed by, and are owned by, the inventor and were never commercially released. The crossing was made by the inventor in his research greenhouse in Bangphra, Thailand in September of 1994.

The new variety was first selected in February of 1999, in a research greenhouse in Bangphra, Thailand belonging to the inventor. After identifying the new variety as a potentially interesting selection, the inventor continued confidential testing and propagation of 'SPCDW1705', assessing stability of the unique characteristics of this variety.

Asexual Reproduction: Asexual March of 2011 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1705' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1705'. These characteristics in combination distinguish 'SPCDW1705' as a new and distinct *Vanda* cultivar:

1. *Vanda* 'SPCDW1705' exhibits numerous large flowers borne on an inflorescence which is carried slightly above the foliage; and
2. *Vanda* 'SPCDW1705' exhibits broad, reniform to orbicular flower petals and broad ovate sepals, all of which are moderately to strongly overlapping; and
3. *Vanda* 'SPCDW1705' exhibits petals and sepals moderately to strongly undulated margins; and
4. *Vanda* 'SPCDW1705' exhibits light purple petals and sepals which are heavily dotted and blotched with a mixture of violet to violet-purple; and 5. *Vanda* 'SPCDW1705' exhibits a labellum with a very dark violet-blue central lobe, and light yellow lateral lobes which are dotted with violet-blue.

BOTANICAL DESCRIPTION OF THE PLANT

Figure 1:
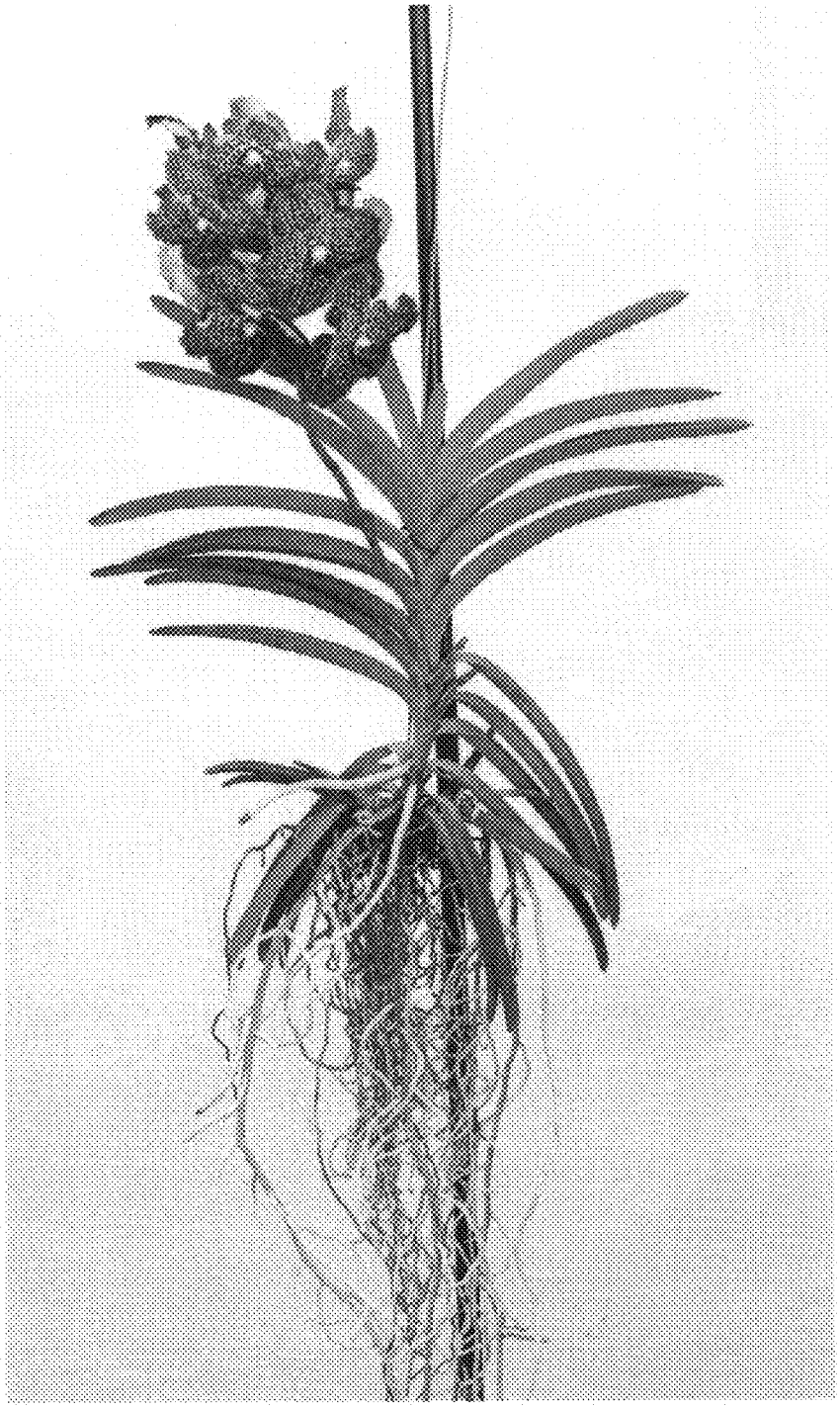
FIG. 1 illustrates, as nearly true as it is reasonably possible to make the same in color photographs of this type, an exemplary plant of 'SPCDW1705' grown in a commercial greenhouse in Honselersdijk, the Netherlands. This plant is approximately 6 years old from the time of mericloning, shown planted in an 8 by 2 cm container.
Figure 2:
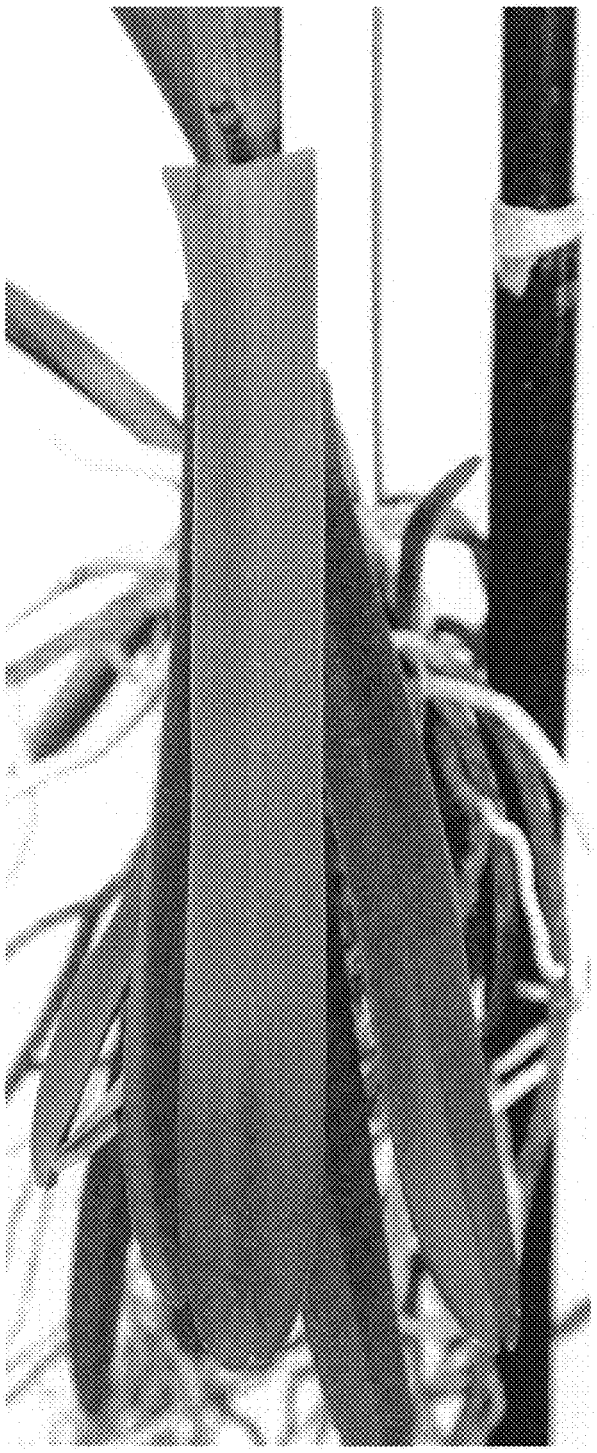
FIG. 2 illustrates, as nearly true as it is reasonably possible to make the same in color photographs of this type, the typical foliage of 'SPCDW1705'.
Figure 3:
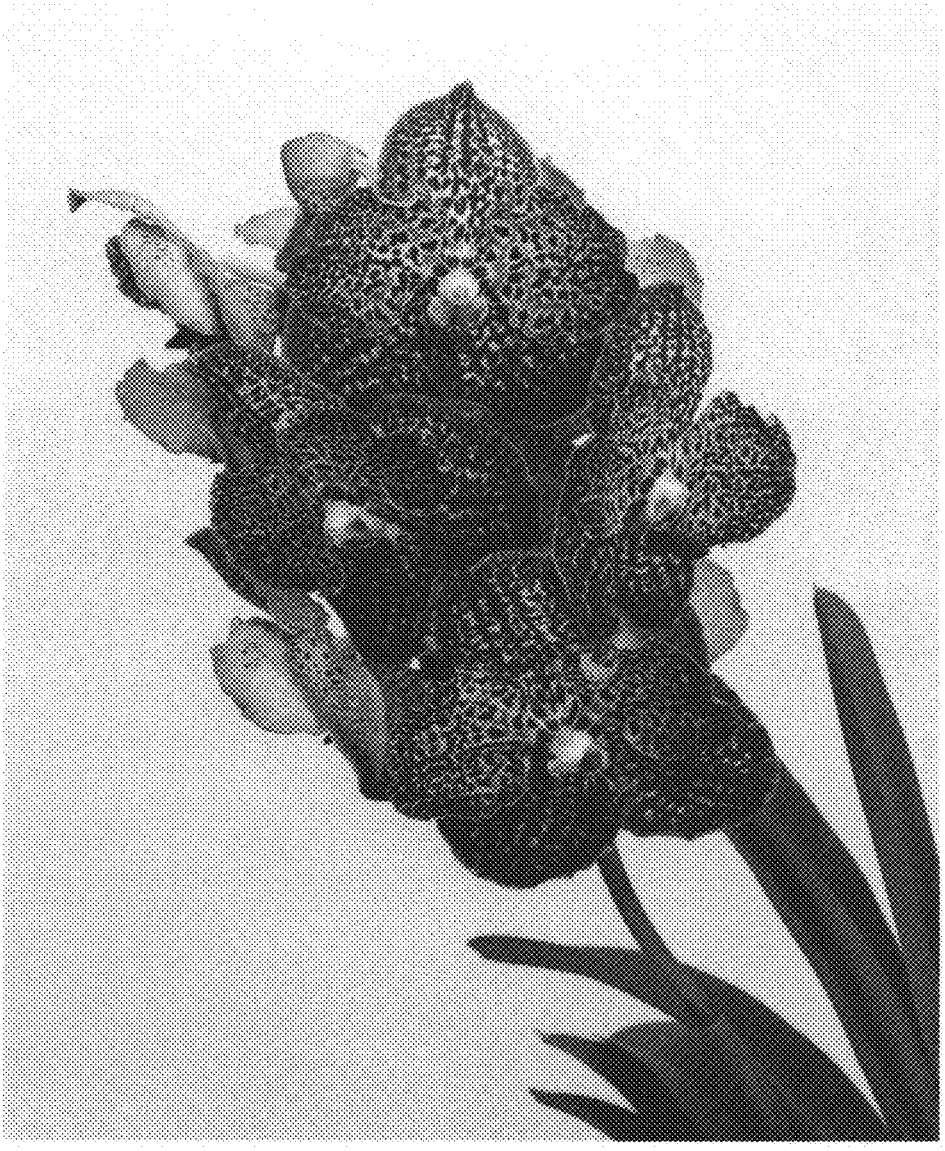
FIG. 3 illustrates, as nearly true as it is reasonably possible to make the same in color photographs of this type, the typical inflorescence of 'SPCDW1705'.
Figure 4:
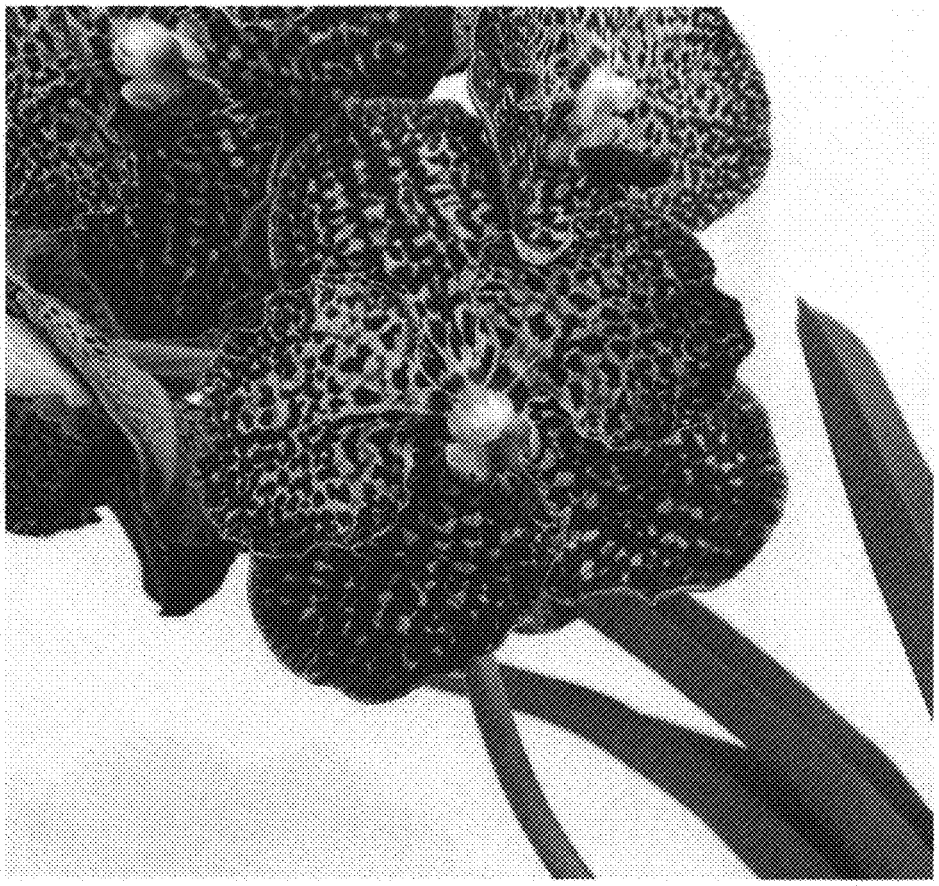
FIG. 4 illustrates, as nearly true as it is reasonably possible to make the same in color photographs of this type, the typical flower of 'SPCDW1705'.

The following observations and measurements made in August of 2018 describe averages from a sample set of six specimens of six year-old 'SPCDW1705' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1705' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'SPCDW1705' and comparisons with the parents and most similar commercial variety of *Vanda* are provided below.

Plant description:

*Growth habit*.—Perennial; monopodial, upright. Single monopodial leafy stem, with flowers carried slightly above the leaf plane; inflorescences growing from the leaf axils.

*Average height from base (plant grown in hanging basket, so no soil line present) to foliar plane*.—45.6 cm.

*Average height from base (plant grown in hanging basket, so no soil line present) to top of floral plane*.—62.8 cm.

*Plant spread*.—Average of 47.2 cm.

*Appropriate container size*.—8 cm by 2 cm rectangular hanging basket.

*Growth rate*.—Moderate.

*Plant vigor*.—Moderate.

*Propagation type*.—Meristematic tissue culture propagation using the base of the leaves.

*Propagation details*.—The time needed from the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.

*Disease and pest resistance or susceptibility*.—Plants have not been observed to be susceptible or resistant to pathogens and pests common to *Vanda*.

*Environmental tolerances*.—Adapt to, at least, USDA Zones 11 and 12 and temperatures as high as 40 degrees Celsius; high tolerance to rain; moderate to high tolerance to wind.

Root system:

*General*.—Moderately to densely rooting; with aerial roots only.

*Dimensions, mature roots*.—87.7 cm long with a diameter of 0.5 cm, on average.

*Texture*.—Very fleshy; non-fibrous.

*Color*.—Greyed-green, nearest to RHS 192C; root apex is yellow-green, RHS 148A.

Stem:

*Branching habit*.—Monopodial; no lateral branches present.

*Number of primary (main) stems per plant*.—One.

*Number of secondary (lateral) branches per plant*.—None.

*Appearance and shape*.—Circular, formed by the leaf sheaths.

*Length*.—25.5 cm.

*Diameter*.—1.0 cm.

*Internode length*.—1.2 cm.

*Luster*.—Matte.

*Aspect, main stem*.—Near vertical.

*Strength*.—Very strong.

*Color, juvenile*.—Yellow-green, nearest to RHS 145D.

*Color, mature*.—In between yellow-green, RHS 145D, and green-white, RHS 157A.

*Color at internodes*.—In between yellow-green, RHS 145D, and green-white, RHS 157A.

*Pubescence*.—Glabrous.

Foliage:

*Arrangement*.—Distichous.

*Dimensions*.—26.5 cm long, excluding the sheath, and 3.0 cm wide.

*Shape of blade*.—Ligulate; moderately to strongly carinate.

*Aspect*.—Moderately curved.

*Apex*.—Unequal praemorse.

*Base*.—Sheathing.

*Sheath dimensions*.—4.0 cm long and 1.6 cm wide, on average.

*Sheath color*.—Yellow-green, nearest to RHS 145A.

*Margin*.—Entire.

*Pubescence, texture and luster of adaxial surface*.—Glabrous, smooth, and matte.

*Pubescence, texture and luster of abaxial surface*.—Glabrous, smooth, and matte.

*Color*.—Juvenile foliage, adaxial surface — Yellow-green, nearest to RHS 144A; darker towards the apex and margins, nearest to RHS 137B. Juvenile foliage, abaxial surface — Nearest to in between green, RHS 143B, and yellow-green, RHS 144A; darker towards the apex and margins, nearest to RHS 137B. Mature foliage, adaxial surface — Green, nearest to RHS NN137A. Mature foliage, abaxial surface — Yellow-green, nearest to in between RHS 146B.

*Venation*.—Pattern — Parallel. Color, adaxial surface — Green, nearest to RHS NN137A. Color, abaxial surface — Yellow-green, nearest to RHS 144B.

*Petiole*.—No petioles present; leaves sessile.

Inflorescence:

*Inflorescence arrangement*.—Axially placed raceme.

*Natural flowering season*.—Autumn into winter.

*Time to flower*.—Approximately 10 months.

*Flowers per inflorescence*.—Average of 12.

*Flowers per plant*.—11 open flowers and 1 flower buds.

*Inflorescence height*.—Approximately 27.2 cm (measured from base of lowest flower to top of upper flower).

*Inflorescence diameter*.—Approximately 22.2 cm.

*Peduncle*.—Dimensions — Approximately 36.0 cm long and 0.65 cm wide. Aspect — Generally at a 30 degree angle to lateral branch axis. Strength — Moderately strong. Texture and luster — Glabrous and matte. Color — Yellow-green, nearest to RHS 145A.

Bud:

*Length*.—Average of 2.7 cm.

*Diameter*.—Average horizontal diameter is 2.2 cm; the vertical diameter is 2.2 cm.

*Shape*.—Cubic, with a deltoid apex which is pointed downward.

*Pubescence, texture and luster*.—Glabrous, smooth and slightly glossy.

*Color*.—Purple, nearest to RHS N77D, and suffused with yellow-green towards the base, nearest to RHS 146D; bud is sparsely dotted purple, nearest to RHS N77A.

Flower:

*Flower type*.—Zygomorphic (orchidaceous), typical shape for the genus *Vanda*.

*Flowering habit*.—Moderately free flowering.

*Shape*.—Zygomorphic, single; consisting of three sepals and three petals, one of which is transformed into a labellum; the two lateral petals strongly overlap the lateral sepals and moderately overlap the dorsal sepal; lateral sepals moderately overlap one another.

*Attitude*.—Flowers are outward-facing to slightly nodding.

*Vertical height*.—Approximately 10.8 cm.

*Diameter*.—Approximately 10.1 cm.

*Depth*.—Approximately 3.9 cm.

*Fragrance*.—No fragrance.

*Lastingness*.—3 weeks, on average.

*Persistent*.—Self-cleaning.

*Petals*.—Quantity of Petals — Three unfused petals; two conventional petals and one labellum. Arrangement — One lateral petal on each side. Length — Approximately 4.6 cm. Width — Approximately 5.0 cm. Shape — Reniform to near orbicular. Apex — Obtuse. Base — Cuneate. Margin — Entire; moderately to heavily undulated. Pubescence, texture and luster of upper surface — Glabrous, velvety and matte. Pubescence, texture and luster of lower surface — Glabrous, velvety and matte. Color when opening, upper surface — White, nearest to RHS 155C, and suffused with purple, and more so towards the margins and apex, nearest to RHS 85D; base of the petal is violet-blue, nearest to RHS N92A. Petals are heavily dotted violet-blue, nearest to RHS N92A; dots at and near the apex are violet, RHS 86A. Color when opening, lower surface — White, nearest to RHS 155C, and lightly suffused with purple towards the margins and apex, nearest to RHS 85C. Petals are sparsely dotted violet-blue, nearest to RHS N92A. Color when fully opened, upper surface — White, nearest to RHS NN155C, and suffused with purple, and more so towards the margins and apex, nearest to RHS 85A; base of the petal is violet-blue, nearest to RHS N92A. Petals are heavily dotted and blotched with a mixture of violet and violet-blue, nearest to RHS 85A, 86B, 86D and N92A. Color when fully opened, lower surface — White, nearest to RHS 155C, and lightly suffused with purple towards the margins and apex, nearest to a mixture of RHS 85A and 86B. Petals are sparsely dotted violet-blue, nearest to RHS N92A. Fading, upper surface — Not fading. Fading, lower surface — Not fading. Venation — Densely reticulate on the upper surface; only the main vein is visible on the lower surface. Venation color, fully opened, upper surface — White, nearest to RHS NN155C, and suffused with purple, and more so towards the margins and apex, nearest to RHS 85A; base of the petal is violet-blue, nearest to RHS N92A. Petals are heavily dotted, and blotched with a mixture of violet and violet-blue, nearest to RHS 85A, 86B, 86D and N92A. Venation color, fully opened, lower surface — Only the main vein is visible; colored violet, nearest the RHS 84C.

*Labellum*.—Shape — Three-lobed; the shape of the lateral lobes is obovate, and the aspect is involute; the shape of the central lobe is broad oblong, and the aspect is moderately revolute. Length — Central lobe — Approximately 1.9 cm. Lateral lobes — Approximately 0.5 cm. Width — Central lobe — Approximately 1.0 cm at the base; 0.8 at the apex. Lateral lobes — Approximately 0.9 cm. Apex — Central lobe — Emarginate. Lateral lobes — Obtuse. Base — Central lobe — Cuneate. Lateral lobes — Cuneate. Margin — Central lobe — Entire; moderately undulated. Lateral lobes — Entire; not undulated. Texture and luster of upper surface — Central lobe — Glabrous, velvety, and matte. Lateral lobes — Glabrous, velvety, and matte. Texture and luster of lower surface — Central lobe — Glabrous, velvety, and matte. Lateral lobes — Glabrous, velvety, and matte. Color when opening, upper surface — Central lobe — Violet, nearest to RHS 86A. Lateral lobes — Green-white, nearest to RHS 157B, and becoming yellow-orange, RHS 14A. Lobes are dotted violet-blue, nearest to RHS N92A. Color when opening, lower surface — Central lobe — Green-white, nearest to in between RHS 157C and 157D, and becoming violet at the upper one-third portion of the lobe, nearest to RHS 86A. Lateral lobes — Green-white, nearest to RHS 157D, and radially striped and suffused with violet, nearest to RHS N88D. Color when fully opened, upper surface — Central lobe — Violet-blue, nearest to RHS N92A. Lateral lobes — Green-white, nearest to RHS 157B, and becoming yellow-orange, RHS 14A, at the base. Lobes are dotted violet-blue, nearest to RHS N92A. Color when fully opened, lower surface — Central lobe — Green-white, nearest to in between RHS 157C and 157D, and becoming violet at the upper one-third portion of the lobe, nearest to RHS N92A. Lateral lobes — Green-white, nearest to RHS 157D, and radially striped and suffused with violet, nearest to RHS N88D. Fading, upper surface — Not fading. Fading, lower surface — Not fading. Venation — No visible venation. Venation color, fully opened, upper surface — Central lobe — No visible venation. Lateral lobes — No visible venation. Venation color, fully opened, lower surface — Central lobe — No visible venation. Lateral lobes — No visible venation.

*Callosities*.—Dimensions — 1.4 cm long and 0.5 cm wide, on average. Color — Violet, nearest to RHS N92A, and fading to a lighter towards the base, nearest to a mixture of RHS 86A and 85D.

*Spurs*.—Quantity — Average of 1. Length — Approximately 0.8 cm. Diameter — Approximately 0.4 cm. Vertical height — Approximately 0.7 cm, at the base. Shape — Short triangular; flattened. Apex — Bluntly acute. Base — Broad cuneate. Pubescence, texture and luster — Glabrous, smooth, and matte. Color — Green-white, nearest to RHS 157D, and radially striped and suffused with violet, nearest to RHS N88D.

*Sepals*.—Quantity — Average of 3 unfused sepals. Arrangement — One dorsal sepal and two lateral sepals. Length — Dorsal sepal — Approximately 5.5 cm. Lateral sepals — Approximately 5.2 cm. Width — Dorsal sepal — Approximately 6.0 cm. Lateral sepals — Approximately 6.0 cm. Shape — Dorsal sepal — Broad ovate. Lateral sepals — Broad ovate. Apex — Dorsal sepal — Obtuse. Lateral sepals — Obtuse. Base — Dorsal sepal — Cuneate. Lateral sepals — Cuneate. Margin — Dorsal sepal — Entire; moderately undulated. Lateral sepals — Entire; moderately undulated. Pubescence, texture and luster, upper surface — Dorsal sepal — Glabrous, velvety, and matte. Lateral sepals — Glabrous, velvety, and matte. Pubescence, texture and luster, lower surface — Dorsal sepal — Glabrous, velvety, and matte. Lateral sepals — Glabrous, velvety, and matte. Color when opening, upper surface — Dorsal sepal — White, nearest to RHS 155C, and suffused with purple, and more so towards the margins and apex, nearest to RHS 85D; base of the petal is violet-blue, nearest to RHS N92A. Sepal is heavily dotted violet-blue, nearest to RHS N92A. Lateral sepals — Green-white, nearest to a mixture of RHS 157C to 157D, and suffused with purple, and more so towards the margins and apex, nearest to RHS N87D. Sepals are heavily dotted violet, nearest to a mixture of RHS 83B and N92A. Color when opening, lower surface — Dorsal sepal — White, nearest to RHS 155C, and lightly suffused with purple towards the margins and apex, nearest to RHS 85C. Sepal exhibits a central purple-violet spot, RHS N82B, and is also sparsely dotted violet-blue, nearest to RHS N92A. Lateral sepals — White, nearest to RHS 155C, and lightly suffused with purple towards the margins and apex, nearest to RHS 85C. Sepals are sparsely dotted violet-blue, nearest to RHS N92A. Color when fully opened, upper surface — Dorsal sepal — White, nearest to RHS NN155C, and suffused with purple, and more so towards the margins and apex, nearest to RHS 85A; base of the petal is violet-blue, nearest to RHS N92A. Sepal is heavily dotted and blotched with a mixture of violet and violet-blue, nearest to RHS 85A, 86B, 86C, 86D and N92A. Lateral sepals — Green-white, nearest to a mixture of RHS 157C to 157D, and suffused with purple towards the margins and apex, nearest to RHS N87D. Sepals are heavily dotted and blotched violet, nearest to a mixture of RHS 83B and N92A. Color when fully opened, lower surface — Dorsal sepal — White, nearest to RHS NN155C, and suffused with purple-violet towards the margins and apex, nearest to a mixture of RHS N82C and N82D. Sepal exhibits a central purple-violet spot, RHS N82B, and is also sparsely dotted violet-blue, nearest to RHS N92A. Lateral sepals — Green-white, nearest to RHS 157B, and suffused with violet towards the margins and apex, nearest to RHS 86C. Sepals are sparsely to moderately dotted violet-blue, nearest to RHS N92A. Fading, upper surface — Not fading. Fading, lower surface — Not fading. Venation — Densely reticulate. Venation color, fully opened, upper surface — Dorsal sepal — White, nearest to RHS NN155C, and suffused with purple, and more so towards the margins and apex, nearest to RHS 85A; base of the petal is violet-blue, nearest to RHS N92A. Sepal is heavily dotted and blotched with a mixture of violet and violet-blue, nearest to RHS 85A, 86B, 86C, 86D and N92A. Lateral sepals — Green-white, nearest to a mixture of RHS 157C to 157D, and suffused with purple towards the margins and apex, nearest to RHS N87D. Sepals are heavily dotted and blotched violet, nearest to a mixture of RHS 83B and N92A. Lateral sepals — Greyed-purple, nearest to RHS N186D. Venation color, fully opened, lower surface — Dorsal sepal — Purple-violet, nearest to RHS N80C. Lateral sepals — Purple-violet, nearest to RHS N80C.

*Pedicels*.—Length — Approximately 5.5 cm. Diameter — Approximately 0.6 cm. Angle — Approximately 80 degree angle to peduncle axis. Strength — Moderate. Texture — Glabrous, axially angled with 5 "ribs", axially twisted (due to resupination). Luster — Moderately glossy. Color — A mixture of purple and white, nearest to RHS 77B, 77D and 155A.

*Bract*.—Quantity — One bract present at the base of each pedicel. Shape — Broad oblong; folded around the base of each pedicel. Dimensions — Average of 1.7 cm long and 1.2 cm wide. Apex — Broad obtuse. Base — Broad cuneate. Margins — Entire. Color, inner surface — Yellow-green, nearest to RHS N144B. Color, outer surface — Yellow-green, nearest to RHS N144B.

Reproductive organs:

*Column*.—Length — Approximately 0.6 cm. Diameter — Approximately 0.8 cm. Color — White, nearest to RHS 155C; the upper surface is suffused with purple, nearest the RHS 77B.

*Ovary*.—Position — Inferior. Diameter — Approximately 0.2 cm. Color — Yellow-green, nearest to RHS 150D.

*Pollinia color*.—Yellow-orange, nearest to RHS 14B.

Seed and fruit: No fruit and seed production has been detected to date.

COMPARISON WITH THE PARENT PLANTS

Plants of the new cultivar 'SPCDW1703' differ from the *Vanda* seed parent, 'S13' (not patented), by the characteristics described in Table 1.

TABLE 1

| Characteristic | 'SPCDW1705' | 'S13' |
|---|---|---|
| Growth habit. | More compact than 'S13'. | Less compact than 'SPCDW1705'. |
| Flowering habit. | More freely flowering. | Less freely flowering. |
| Flower size. | Larger than 'S13'. | Smaller than 'SPCDW1705'. |
| General coloration of the petals and sepals when fully opened. | Darker violet-blue. | Lighter violet-blue. |
| Occurrence of spotting on the lateral petals. | More densely spotted. | Less densely spotted. |

Plants of the new cultivar 'SPCDW1703' differ from the *Vanda* pollen parent, *Vanda* 'NUR' (not patented), by the characteristics described in Table 2.

TABLE 2

| Characteristic | 'SPCDW1705' | 'NJR' |
|---|---|---|
| Vigor; rate of growth. | Easier to propagate and faster growing than 'NJR'. | More difficult to propagate and slower growing than 'SPCDW1705'. |
| Size of the lateral petals and sepals. | Larger than 'NJR'. | Smaller than 'SPCDW1705'. |
| Size of the lateral petals and sepals. | Larger and broader than 'NJR'. | Smaller and more narrow than 'SPCDW1705'. |
| Overlapping of petals and sepals | More overlapping than 'NJR'. | Less overlapping than 'SPCDW1705'. |
| General coloration of the petals and sepals when fully opened. | Darker violet-blue. | Lighter violet-blue. |
| Overlaid color pattern of the sepals. | More spotted than reticulated. | More reticulated than spotted. |

COMPARISON WITH THE MOST SIMILAR *VANDA* CULTIVAR KNOWN TO THE INVENTOR

Plants of the new cultivar 'SPCDW1705' are similar to the cultivar, *Vanda* 'SPCDW0904' (European Community Plant Variety Rights grant number 297775). A comparison of 'SPCDW1705' with *Vanda* 'SPCDW0904' is described in Table 3.

TABLE 3

| Characteristic | 'SPCDW1705' | 'SPCDW0904' |
|---|---|---|
| Petal undulation. | More heavily undulated. | Not as undulated. |
| General coloration of the petals and sepals when fully opened. | Dark violet-blue. | Dark red-purple. |
| Width of the central lobe of the labellum. | More narrow than 'SPCDW0904'. | Wider than 'SPCDW1705'. |
| General coloration of the column. | White and suffused with violet. | Cream. |

That which is claimed is:

1. A new and distinct variety of *Vanda* plant named 'SPCDW1705', substantially as described and illustrated herein.

* * * * *